United States Patent
Kantorovich et al.

(10) Patent No.: US 7,022,076 B1
(45) Date of Patent: Apr. 4, 2006

(54) BONE VELOCITY DETERMINATION

(75) Inventors: Edward Kantorovich, Rehovot (IL); Yehuda Niv, Nes-Ziona (IL)

(73) Assignee: Sunlight Medical Ltd., Tel-Aviv (IL)

( * ) Notice: Subject to any disclaimer, the term of this patent is extended or adjusted under 35 U.S.C. 154(b) by 0 days.

(21) Appl. No.: 09/831,396

(22) PCT Filed: Oct. 24, 1999

(86) PCT No.: PCT/IL99/00561

§ 371 (c)(1),
(2), (4) Date: May 7, 2001

(87) PCT Pub. No.: WO00/28316

PCT Pub. Date: May 18, 2000

(30) Foreign Application Priority Data

Nov. 8, 1998 (IL) ........................................ 126956
Sep. 8, 1999 (IL) ........................ PCT/IL99/00489

(51) Int. Cl.
*A61B 8/12* (2006.01)

(52) U.S. Cl. ..................................... 600/449

(58) Field of Classification Search ................ 600/449, 600/437, 450, 451, 452, 407, 528; 73/584–648; 181/101; 367/87, 7, 14
See application file for complete search history.

(56) References Cited

U.S. PATENT DOCUMENTS

| | | | |
|---|---|---|---|
| 4,048,986 A | 9/1977 | Ott | |
| 4,819,753 A * | 4/1989 | Higo et al. | 600/586 |
| 4,823,807 A | 4/1989 | Russell et al. | |
| 4,913,157 A | 4/1990 | Pratt, Jr. et al. | |
| 5,024,239 A | 6/1991 | Rosenstein | |
| 5,143,069 A | 9/1992 | Kwon et al. | |
| 5,143,072 A | 9/1992 | Kantorovich et al. | |
| 5,396,891 A * | 3/1995 | Whitney et al. | 600/449 |
| 5,402,781 A | 4/1995 | Dimarogonas | |
| 5,651,363 A | 7/1997 | Kaufman et al. | |
| 5,806,520 A | 9/1998 | Berger et al. | |
| 5,807,250 A | 9/1998 | Ohtomo et al. | |
| 5,853,005 A * | 12/1998 | Scanlon | 600/459 |
| 6,029,078 A * | 2/2000 | Weinstein et al. | 600/407 |

FOREIGN PATENT DOCUMENTS

| | | |
|---|---|---|
| EP | 0 341 969 | 11/1989 |
| EP | 0 626 656 | 11/1994 |

(Continued)

OTHER PUBLICATIONS

Takatoshi, I.; Patent Abstracts of Japan, vol. 17, No. 446 (C-1098) & JP 05-103804; Aug. 17, 1993.

(Continued)

*Primary Examiner*—Daniel Robinson
(74) *Attorney, Agent, or Firm*—Fenster & Company

(57) ABSTRACT

A method of determining an acoustic velocity in a bone, comprising:
  transmitting, from a location adjacent a first in-vivo bone, an acoustic wave having a wavelength about the same or smaller than a cross-section of the bone, which cross-section is perpendicular to a main travel direction of said acoustic wave in said bone;
  receiving said acoustic wave at a location adjacent a second in-vivo bone; and
  determining an acoustic velocity of at least a portion of at least one of the first and second bones, from a travel time of said wave through said first and second bones and at least one joint between said bones.

30 Claims, 6 Drawing Sheets

FOREIGN PATENT DOCUMENTS

| | | |
|---|---|---|
| EP | 0 797 952 | 10/1997 |
| FR | 2 768 322 | 3/1999 |
| WO | WO 95/26160 | 10/1995 |
| WO | WO 97/13145 | 4/1997 |

OTHER PUBLICATIONS

Sun, Y.N. et al.; "A Computer System for Skeletal Growth Measurement;" Computers and Biomedical Research; vol. 27; 1994; pp. 2-12; XP002067754.

* cited by examiner

BONE VELOCITY DETERMINATION

RELATED APPLICATION

This application is a U.S. national filing of PCT Application No. PCT/IL99/00561, filed Oct. 24, 1999.

FIELD OF THE INVENTION

The present invention relates to non-invasive measurement of the mechanical properties of bone.

BACKGROUND OF THE INVENTION

It is known in the art that the velocity of a sound wave in a material depends on the mechanical properties of the material.

Bone velocity measurement typically uses one of two methods. In a first method, an ultrasound wave is transmitted across a bone, in a direction transverse to its axis, for example across the phalanx or across an ankle. In a second method, an ultrasonic wave is transmitted from a skin surface generally parallel to the bone, to the bone, and its reflections or emissions from the bone, at a distance along the axis of the bone, are detected.

In order to perform in vivo ultrasonic measurements of the mechanical properties of a bone, it is necessary to transmit an ultrasonic wave through the soft tissue surrounding the bone. Unfortunately, the thickness of the soft tissue varies along the length of the bone. Also, the soft tissue velocity is not a constant value for all soft tissues. These variations can affect the accuracy of the ultrasound propagation time measurement through the bone. Typically, the variations in thickness of the soft tissue and its velocity are either ignored or an attempt is made to cancel the effects of the soft tissue.

For example, U.S. Pat. No. 5,143,072 and PCT publication WO 97/13145, the disclosures of which are incorporated herein by reference, describe methods of overcoming the effects of the unknown thickness of the intervening soft tissue, by ensuring that the measurements are taken when the portion of the path which passes through soft tissue is of a same length for different measurements or by determining a soft tissue velocity.

U.S. Pat. No. 4,819,753, the disclosure of which is incorporated herein by reference, describes a method of analyzing the status of a hip implant, by detecting the time of flight of vibrations from a hammer hitting the bone, at a knee and outside a spina iliaca posterior superior of a pelvis. In this method, very low frequency acoustic waves are generated and detected, between about 50 Hz and 2 kHz.

U.S. Pat. No. 4,048,986, the disclosure of which is incorporated herein by reference, describes a method of diagnosing or identifying a person by measuring the effect on a polarization of an ultrasonic wave which travels between an elbow and a wrist or between a knee and an ankle. Audio-frequency waves appear to be suggested.

SUMMARY OF THE INVENTION

It is an object of some preferred embodiments of the invention to reduce uncertainties in bone velocity determination caused by unknown thickness of overlying soft tissue.

An object of some preferred embodiments of the invention is to measure changes in mechanical properties of bones, especially in trabecular bone tissue.

One aspect of some preferred embodiments of the invention is that an ultrasonic wave for measuring bone velocity is transmitted through a joint between two bones. In a preferred embodiment of the invention, the wave is transmitted from the pelvis to a knee, thereby passing through both a pelvic bone and a hip bone. Preferably a moderately high ultrasonic frequency is used, so that the wavelength is smaller than a cross-sectional diameter of a bone or at most two or three times its size, for example about 160 kHz for a femoral neck. Theoretically, if the cross-sectional diameter is greater than about 0.7 time the wavelength, the velocity of the wave is about the same as if the cross-section was infinite. Also, the presence of small metal pins may have a negligible effect, for two possible reasons. First, if the diameter of the pin is small, the relatively low frequencies used propagate through the pin much slower than high frequencies. Additionally or alternatively, a reflection of waves from the pin is expected due to a usually large difference in refractive index between them, so there will be no effect on a shortest travel time.

An aspect of some preferred embodiments of the invention is that an acoustic velocity of the bone is measured along a main axis of a bone, preferably, along an entire bone. In a preferred embodiment of the invention, the bone is a femur. Preferably, the wave travels through the hip joint and measures the acoustic velocity along the femoral neck and/or a trochanter.

An aspect of some preferred embodiments of the invention relates to using distanced ultrasonic sources and detectors, to measure local acoustic characteristics of bone or soft tissue. In a preferred embodiment of the invention, at least two paths are set up, for example between one source, such as a transmitter, and two detectors. The distance between the source and the detectors causes these paths to substantially overlap along most of their length. Preferably, the non-overlapping portion is related to the geometrical arrangement of the detectors (and/or the transmitters) and is near the detectors (or the transmitters, in a swapped configuration with a remote detector and local transmitters). Thus, local acoustic characteristics of the bone can be determined by comparing signals at the two detectors. Some non-acoustic characteristics of the bone, such as Young's modulus, can be estimated from these measurements. In one example, a speed of sound in a local portion of bone is detected by subtracting the relative or absolute-times of arrival of a signal at the two detectors. In a preferred embodiment of the invention, two or more sets of paths are used, and the results for the two sets of paths are compared to correct for various types of errors and/or allow a more exact local measurement. In one example, a more exact speed of sound is determined in the presence of an unknown angle between the bone and the detector.

In a preferred embodiment of the invention, the source(s) and the receiver(s) are not coupled together, for example being separate probes, so there is virtually no parasitic coupling between them. In some embodiments described herein, there is no need for an exact knowledge of the relative positions of the source(s) and the receiver(s), so use of such separate probes is made easier. By positional relationship is meant the relative position of the probes. Of course, in typical applications, a physician will be aware approximately where each probe is coupled to the body, but exact knowledge of the relative placement is not required in some embodiments of the invention.

Another aspect of some preferred embodiments of the invention relates to substantially direct measurement of a trabecular portion of the bone, by ignoring and/or subtracting propagation time spent in a cortical portion. When measuring along an axial dimension of the bone, the percentage of travel through the cortical portion can be made relatively small as compared to travel through the trabecular portion. Additionally or alternatively, in certain configurations, two adjacent paths may have substantially the same cortical travel portions and different trabecular travel portions, so a difference between travel time along the two paths is expected to be mainly due to the trabecular bone. By subtracting the path lengths and dividing by the difference in time of flight, a trabecular velocity is preferably determined.

There is thus provided in accordance with a preferred embodiment of the invention, a method of determining an acoustic velocity in a bone, comprising:

transmitting, from a location adjacent a first in-vivo bone, an acoustic wave having a wavelength about the same or smaller than a cross-section of the bone, which cross-section is perpendicular to a main travel direction of said acoustic wave in said bone;

receiving said acoustic wave at a location adjacent a second in-vivo bone; and determining an acoustic velocity of at least a portion of at least one of the first and second bones, from a travel time of said wave through said first and second bones and at least one joint between said bones. Preferably, said locations have an unknown positional relationship. Alternatively, said locations have a known positional relationship.

In a preferred embodiment of the invention, said receiving and said transmitting comprise receiving and transmitting using mechanically coupled acoustic elements. Alternatively, said receiving and said transmitting comprise receiving and transmitting using mechanically uncoupled acoustic elements.

There is also provided in accordance with a preferred embodiment of the invention, a method of determining a characteristic of a bone, comprising:

transmitting, from a location adjacent a first in-vivo bone, an acoustic wave having a frequency of at least 20 kHz;

receiving said acoustic wave at a location adjacent a second in-vivo bone; and determining at least one acoustic characteristic of at least a portion of at least one of the first and second bones, from a travel time of said wave through said first and second bones and at least one joint between said bones. Preferably, said acoustic characteristic comprises acoustic velocity. Alternatively, said acoustic characteristic comprises acoustic attenuation. Alternatively, said acoustic characteristic comprises polarization properties.

In a preferred embodiment of the invention, said acoustic characteristics are determined for a plurality of wavelengths, to estimate a frequency dependent variation thereof. Alternatively or additionally, the joint is articulated.

In a preferred embodiment of the invention, said first and second bones are interconnected by at least a third bone and wherein said at least one joint comprises at least one joint interconnecting said first bone and said at least third bone and at least a second joint interconnecting said at least third and said second bones. Preferably, said at least a third bone comprises at least two bones interconnected by a joint, through which the wave travels.

In a preferred embodiment of the invention, said wave travels between an elbow and a finger. Alternatively, said wave travels between an elbow and a knuckle. Alternatively, said wave travels between a knee and an ankle. Alternatively, said wave travels between a trochanter and an pelvis. Alternatively, said wave travels between two hips. Alternatively, said wave travels along a rib. Alternatively, said wave travels along a portion of a skull. Alternatively, said bones comprise spinal vertebra.

In a preferred embodiment of the invention, receiving the acoustic wave comprises receiving at least a second acoustic wave, which second wave has a path substantially overlapping a path in bone of said first wave for a significant portion of its length. Preferably, the two waves are received using a single receiver and are generated at two different locations. Alternatively, the two waves are received using two receivers and are generated at a single location. Preferably, a line interconnecting said two receivers is not parallel to a surface of bone underlying the two receivers.

In a preferred embodiment of the invention, said travel time comprises a relative travel time of said two waves. Alternatively or additionally, said two waves are generated substantially simultaneously. Alternatively; said two waves are generated as a single source wave. Alternatively, said two waves are generated at a time delayed relative to each other.

In a preferred embodiment of the invention, the method comprises repeating said transmitting and said receiving for at least a second acoustic wave, traveling in a direction substantially opposite a traveling direction of said wave, to determine local acoustic bone characteristics at an area which is traversed by both of said waves.

There is also provided in accordance with a preferred embodiment of the invention, a method of determining an acoustic bone characteristic, comprising:

transmitting an acoustic wave from a first location adjacent a first bone;

receiving said acoustic wave at at least two locations adjacent a second bone, near each other, said locations being significantly distanced from said first location, such that said wave travels substantially overlapping paths from said first location to a location near said two locations; and determining an acoustic characteristic of the bone adjacent said two locations from said received signals.

There is also provided in accordance with a preferred embodiment of the invention, a method of determining an acoustic bone characteristic, comprising:

transmitting an acoustic wave from a first location adjacent a body;

receiving said acoustic wave at at least two locations adjacent a bone, near each other, said locations defining a line non-parallel to the bone surface and significantly distanced from said first location, such that said wave travels substantially overlapping paths from said first location to a location near said two locations; and determining an acoustic characteristic of the bone adjacent said two locations from said received signals. Preferably, said first location is adjacent said bone. Alternatively, said first location is adjacent a different bone.

In a preferred embodiment of the invention, said transmitting and said receiving utilize two mechanically uncoupled elements. Alternatively, said transmitting and said receiving utilize two mechanically coupled elements. Alternatively or additionally, said characteristic comprises a trabecular velocity of the bone. Alternatively or additionally, said characteristic comprises a cortical velocity of the bone. Alternatively or additionally, the method further comprises receiving a second wave at or near said two locations from a second source at a second location, significantly displaced from said two locations and using said received second wave in determining said characteristic. Preferably, said second significantly displaced source is on a substantially opposite side of said at least two locations, from said first location.

In a preferred embodiment of the invention, all of said locations are not collinear. Alternatively or additionally, all of said locations are not coplanar.

There is also provided in accordance with a preferred embodiment of the invention, a method of determining a property of a bone, comprising:

transmitting an acoustic wave having a frequency of above 20 kHz along an axis of said bone, through at least a core thereof;

receiving said wave after said travel; and analyzing said received wave to determine at least one acoustic characteristic of said bone. Preferably, said acoustic characteristic comprises an acoustic velocity.

There is also provided in accordance with a preferred embodiment of the invention, a method of bone velocity measurement, comprising:

transmitting at least one acoustic wave into a bone at a first location;

receiving said wave at at least two locations outside said bone, after is passes through said bone, wherein said first location and said at least two locations are not collinear; and determining a trabecular velocity of said bone from said received wave. Preferably, said bone comprises an ankle bone.

There is also provided in accordance with a preferred embodiment of the invention, a method of determining an acoustic velocity in a bone, comprising:

transmitting an acoustic wave from a first location adjacent an in-vivo bone;

receiving said acoustic wave at a second location adjacent the bone, which second location has an unknown positional relationship relative to said first position; and determining an acoustic velocity of at least a portion of said bone, from a travel time of said wave between said first and said second positions. Preferably, receiving comprises receiving using two receivers. Preferably, there is a difference in time of receipt of the wave by said two receivers, and determining comprises determining from said time difference.

There is also provided in accordance with a preferred embodiment of the invention, apparatus for determining an acoustic velocity in at least a portion of an in-vivo bone, comprising:

a transmitter for generating acoustic signals;

at least one receiver, mechanically uncoupled to said transmitter, for receiving said generated acoustic signals after they travel through a bone; and circuitry for determining an acoustic velocity in said bone responsive to said received wave. Preferably, said circuitry determines said velocity responsive to a relative arrival time of said wave. Alternatively or additionally, said at least one receiver comprises at least two receivers. Preferably, there is a difference in time of receipt of the wave by said two receivers, and determining comprises determining from said time difference.

BRIEF DESCRIPTION OF THE DRAWINGS

The invention will be more clearly understood by reference to the following description of preferred embodiments thereof in conjunction with the figures, wherein identical structures, elements or parts which appear in more than one figure are labeled with the same or similar numeral in all the figures in which they appear, in which.

DETAILED DESCRIPTION OF PREFERRED EMBODIMENTS

Figure 1A:
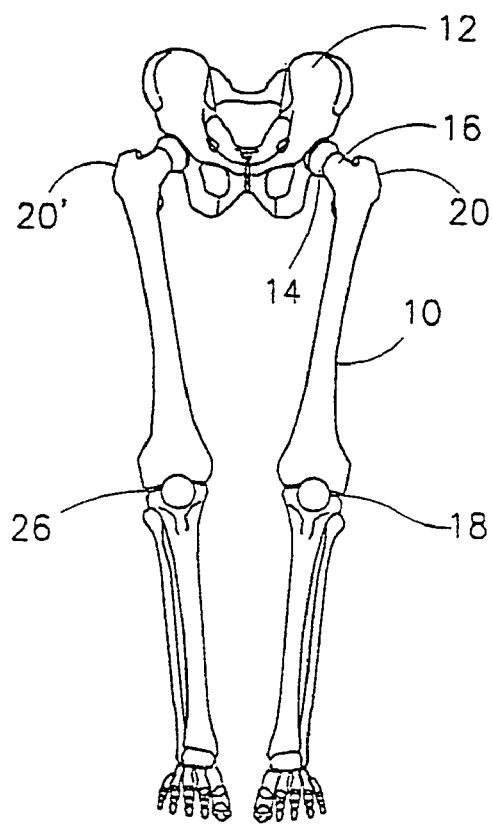
FIGS. 1A, 1B and 1C illustrate a method of femoral measurement in accordance with a preferred embodiment of the invention.
Figure 1B:
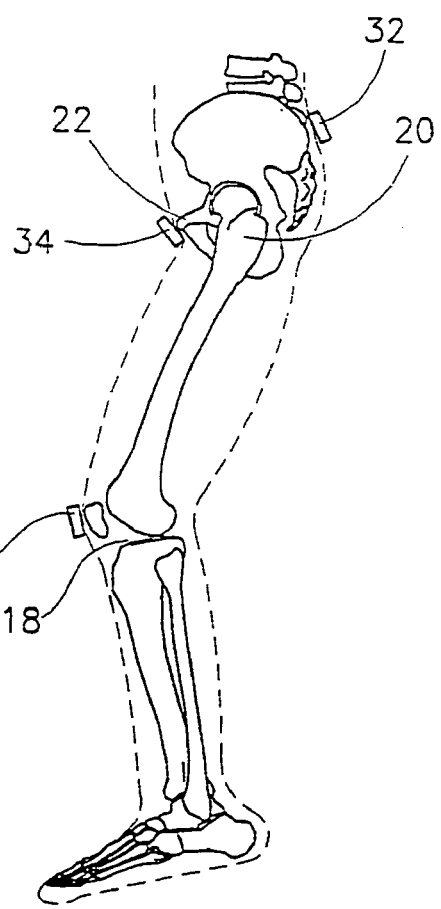

FIGS. 1A and 1B illustrate a femoral measurement in accordance with a preferred embodiment of the invention. A femur 10 is connected to a pelvis 12 at a hip joint 14 and to a calf at a knee joint 18. Hip 10 generally comprises a femoral neck 16, which is not collinear with the rest of hip 10, and is angled at a trochanter 20. FIG. 1B is a side view of FIG. 1A, with a dotted line indicating a general outline of soft tissue which covers the bones shown in FIG. 1A. In a preferred embodiment of the invention, ultrasonic transducers are located at places where the thickness of underlying soft tissue is minimal and/or has a small variation between subjects, for example, at knee 18 (transducer 30), at the trochanter 20 (transducer 32) in the back of pelvis 12 and/or at a pubic area 22 (a transducer 34). In another preferred embodiment of the invention ultrasonic transducers may be placed at the two opposite trochanters, 20 and 20', to determine a velocity between the two trochanters. In various preferred embodiments of the invention, the selection of which of the transducers are transmitters, which are receivers and which are both, is a product deign consideration. Generally, only a single transmitter and a single receiver are required to measure a time of flight between two points. Although only measurement along one direction is generally necessary, in some cases, measurements in two directions may also be taken. Also, in some cases, measurement in one direction may be better (e.g., lower noise) than a measurement in the other direction.

Figure 1C:
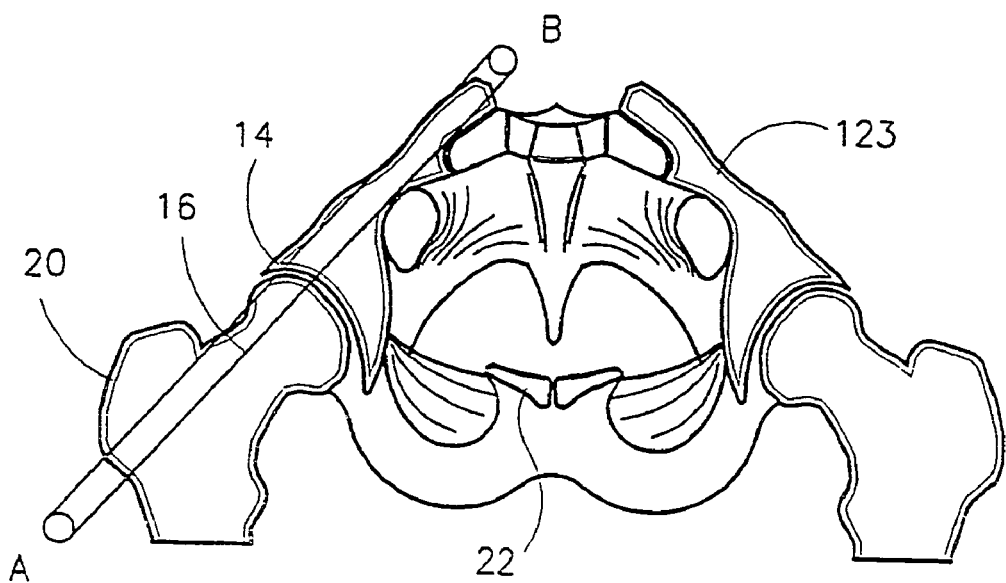
Figure 3:
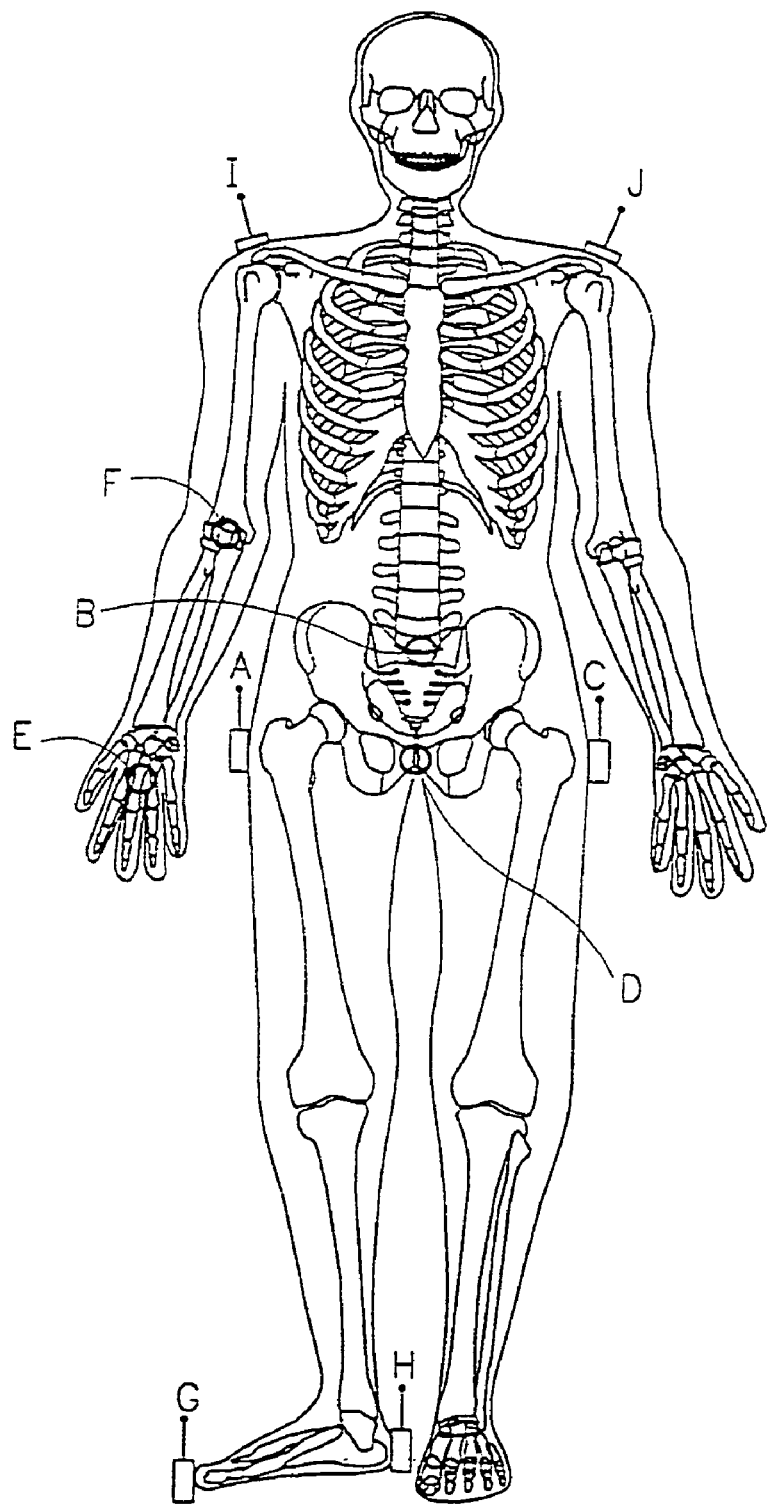
FIG. 3 illustrates various points on a body at which bone velocity may be measured in accordance with a preferred embodiment of the invention.

FIG. 1C is a cross-sectional illustration of the pelvic area, showing a path which may be taken by an ultrasonic beam which travels between a location A and a location B (locations shown also in FIG. 3).

In a preferred embodiment of the invention, a time of flight of an ultrasonic wave is measured between two of the above transducers, whereby a bone of interest lies along a path taken by the ultrasonic wave. Preferably, the path includes hip joint 14. Alternatively or additionally, only a path in the pelvis is measured, for example between the pubic area 22 and location A or between location A and its mirror location on the other side of the pelvis. Alternatively or additionally, the path includes all of pelvis 12, for example by placing transducer 32 at a location "B" on the side of the pelvis opposite location A. Alternatively or additionally, the path includes both femurs, for example by measuring between a knee 26 (FIG. 1A) and knee 18. Alternatively or additionally, a transmitter (or a receiver) is placed at a central location 27 in order to measure times for both hips (for waves to or from transducers at knee 18 and knee 26).

In a preferred embodiment of the invention, an additional receiver and/or transmitter may be placed at one or more locations along femur 10, to determine times of flight to a middle of the femur.

It should be appreciated that the path of the ultrasonic wave in the bone is not straight, as the bone itself is not straight (e.g., a femur, a rib or a jaw bone). Also, the fastest path along the bone may not be the shortest Euclidean one.

The wavelength of acoustic waves is equal to the speed of sound divided by their frequency. For a given speed of sound, which is the property of the material through which the waves travel, the higher the frequency the smaller the wavelength. However, acoustic waves are attenuated along their travel, and higher frequencies are usually attenuated more. In a preferred embodiment of the invention, the frequency used is an ultrasonic frequency, preferably above 20 kHz, above 40 kHz above 60 kHz, between 100 kHz and 400 kHz, or even over 400 kHz. Alternatively, lower frequencies may be used, for example, below 20 kHz, below 16 kHz, below 10 kHz or below 4 kHz. Some of these frequency may be more useful in embodiments described herein other than this one. In a preferred embodiment of the invention, the frequency is selected responsive to the bone being measured. Preferably, the frequency is selected to be low enough so that the attenuation by the travel through the bone, soft tissue and/or through the joint is not too high relative to a noise level of the measurement system. Alternatively or additionally, the frequency is selected to be high enough so that the wavelength is small compared to the cross-sectional diameter of the bone or bones through which the wave travels, such that the wave travels substantially only through the bone and not through the soft tissue surrounding it. In a preferred embodiment of the invention, the frequency is such that the bone cross-sectional diameter (preferably at the middle of the bone and/or its average) is approximately the same as the wavelength or at most smaller than a quarter or a third of the wavelength of the wave. Alternatively, the wavelength is significantly smaller than the bone cross section.

It should be appreciated that in some preferred embodiments of the invention most of the travel time is in the bone and not in the soft tissue, so the travel time in the soft tissue has a small effect on the total travel time. Preferably, the soft tissue (thickness) is ignored in the measurement. Alternatively or additionally, the soft tissue thickness is measured, for example by acoustic imaging or by measuring a time of flight for a reflection from the bone, and the travel time is subtracted. Alternatively or additionally, a soft tissue velocity is estimated, for example, to be about 1500 m/s.

In a preferred embodiment of the invention, the travel time is mostly dependent on the slow bone portions, i.e., those bone portions with the lowest strength, which portions are often the bone portions of interest.

In a preferred embodiment of the invention, the time of flight is measured by determining the first arriving acoustic wave. Alternatively, the time of flight is determined by correlating a received wave with the transmitted wave, or by correlating two received waves for example when transmitting at the pubic region and receiving at knee 26 and 18. Thus, in some cases, only a difference is determined.

Alternatively or additionally to measuring a time of flight, changes in polarization of the transmitted wave may also be measured, possibly requiring specialized polarization sensor or pairs of detectors for measuring small phase differences between the detector pair elements. Alternatively or additionally, a frequency dispersion effect of the bone travel on the wave may be measured. Alternatively or additionally, a frequency transfer function (power spectrum) and/or attenuation function may be measured.

In a preferred embodiment of the invention, the transmitted wave is a pulsed wave, for example having a duty cycle of less than 30%, 20%, or 10%. Alternatively, the wave is a continuous or near continuous wave. Preferably, the wave comprises a narrow-band-frequency wave, for example having a bandwidth of less than 60%, 40% or 30% of its center frequency. Alternatively or additionally, a wide-band-frequency wave is used, for example having a bandwidth of more than 80%, 100% or 120% of its center frequency. Alternatively or additionally, a temporal envelope, having frequency and/or amplitude characteristics, with a temporal length of more than one wavelength is overlaid on the wave.

In one example, a 2 microsecond pulse having a center frequency of 160 kHz is used, this yields a bandwidth of about 500 kHz.

In a preferred embodiment of the invention, the wave is transmitted into the bone at an angle substantially normal to the bone surface, to increase the efficiency of the transmission of the wave and/or to reduce the effects of overlying tissue. Alternatively or additionally, the wave is transmitted in a direction parallel to the bone's long axis. A combination of the two preferred transmission methods often dictates that the wave be transmitted at a joint, usually when the joint is bent.

An apparatus in accordance with a preferred embodiment of the invention preferably comprises a transmitter and a receiver mounted on a "U" shaped frame. Alternatively, at least one of the ultrasonic elements may be mounted on a curved segment attached to the frame, to better fit around a leg or a pelvis. In a preferred embodiment of the invention, at least one of the transducers is movable along the base of the frame and fastenable in place. In use, the transmitters are preferably located at the desirable locations and then fastened in place. The measurements are taken, preferably by sampling directly into a computer. The distance between the transmitters is preferably measured off the frame, preferably automatically, for example using methods known in the art (e.g., optical or linear encoders). Alternatively or additionally, the distance is determined by measuring a time of flight between the transmitter and the receiver in the material of the frame (which has a known velocity) or in the air (which has a known velocity). Alternatively, a fixed frame is used, having a know distance between the transducers. In a preferred embodiment of the invention, at least one of the transducers is mounted to a bed, on which a patient may lie and/or to which the patient may be fastened.

It should be appreciated that the travel time in the frame is generally much shorter than the travel time in the bone so the frame travel time does not usually interfere with detecting the wave which travels through the bone. Alternatively or additionally, the ultrasonic elements are mounted onto the frame using dampers which absorb ultrasonic waves, so substantially no waves will travels through the frame.

Alternatively or additionally, an apparatus may comprise independent transducers which include position sensors mounted thereon. Thus, their relative positions may be measured relative to a base station and/or directly relative to each other. Preferably RF position or distance measurement is used. Alternatively or additionally, airborne ultrasonic position and/or distance sensing is used, possibly using the same transducers.

Alternatively, the distance between the transducers is not determined a-priori.

An alternative apparatus utilizes a table and clamping receiver and transmitter elements. A patient is laid on a table and the transmitters and/or receivers are arranged around the patient and in contact therewith in a desired configuration and then locked in place. In one embodiment, the receivers and transmitters have a magnetic locking clamp which when activated adheres to a metallic table. Alternatively or additionally, at least one of the receivers and/or transmitters is hand-held or attached directly to the patients body, for example using adhesive, vacuum or a strap. It should be noted that a pair of receivers can be emulated by moving a single receiver between measurements. In a preferred embodiment of the invention, the patient is not laid directly on the table, rather, the patient, or at least a limb of interest are laid on a raised narrow support. The fat of the limb then hangs down over the sides of the support, allowing a closer and more reproducible access to the bone.

In a preferred embodiment of the invention, the time of flight measurements are used for comparison studies, for example, between patients, preferably using a table of expected values; between multiple measurements of a single patient over time, preferably utilizing tattoo markings on the patient to mark the locations at which transducers are placed; and/or between opposing limbs of a same patient. As can be appreciated, in some of these cases, it is not necessary to know an exact speed of sound. Rather, it is enough to detect a change (absolute and/or relative) in a time of flight.

In a preferred embodiment of the invention, the measurements of time of flight are used in a group comparison method. For example, for each age group/disease stage, one or more typical velocity ranges are determined. When a patient is tested, the determined velocity is compared to the range expected in the age group/disease stage. A "T" score may be defined, to describe the relationship, with, for example, T=(measured velocity−average velocity in "fastest" age group)/(standard deviation of velocity in the "fastest" age group). Typically, the fastest age group is between 30 and 45. The units of the "T" score are standard deviation units and are usually negative, especially for diseased bone.

Figure 2:
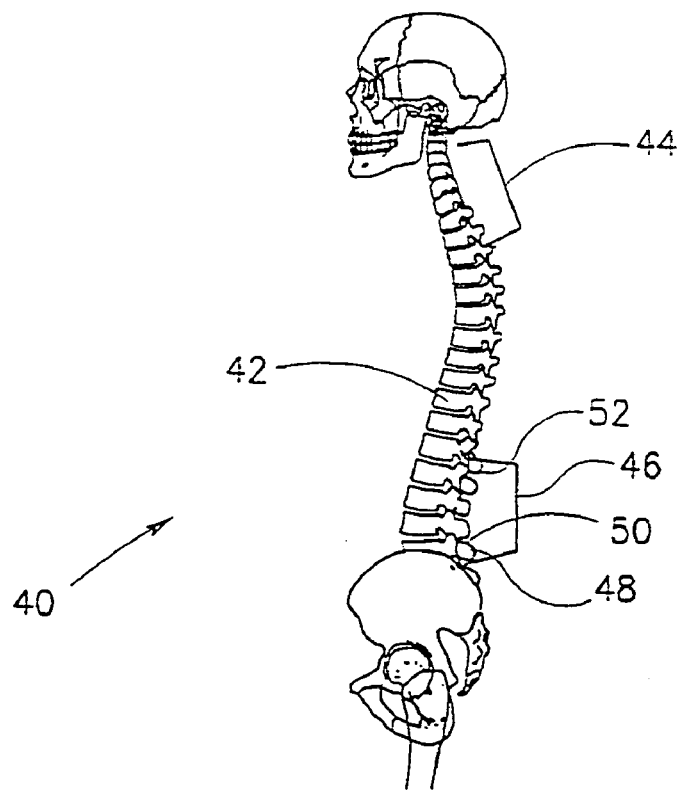
FIG. 2 illustrates a spinal measurement, in accordance with a preferred embodiment of the invention.

FIG. 2 illustrates a spinal measurement, in accordance with a preferred embodiment of the invention. A patient 40 generally has a spine 42, with two special areas of interest usually being defined, a lumbar region 46 and a cervical region 44. In a preferred embodiment of the invention, the time of flight is measured between two vertebra, for example a vertebra 48 and a vertebra 52 in lumbar region 46. Alternatively or additionally, the time of flight in a single vertebra may be measured. Alternatively or additionally, the time of flight along a significant portion of spine 42, for example half of the spine, may be measured.

It should be noted that depending on the frequency used, several paths are possible between two adjacent vertebra. In a first path, the ultrasonic wave travels between the spinal processes of the vertebra, bridging a considerable amount of soft tissue. In a second path, the wave travels through the main part of the backbone, through the spinal disks. A third possible path is along soft tissues that surround the spine. The first and second paths are differentiated by two features of the paths. One feature is that the amount of soft tissue in the second path is smaller than in the first path. Another feature is that the dimensions of the vertebra are larger in the second path than in the first. In a preferred embodiment of the invention, the two paths may be chosen between by appropriately selecting an ultrasonic frequency. A low frequency will not be able to travel as fast in the bone portion of the first path as in the bone portion of the second path. In a preferred embodiment of the invention, a high enough frequency is used, for example 40 kHz, so that the third, soft tissue path, is slower than at least one of the other two paths. Preferably, a time of arrival window mechanism is used to differentiate between the travel along the two paths. Such a relatively low frequency may also be required to overcome the high attenuation caused by the existence of an extra joint for every additional vertebra measured.

In a preferred embodiment of the invention, the travel times may be compared between groups of vertebrae, for example between (L1–L5) and (T1–T12). Preferably the groups comprises same types of vertebrae. Alternatively or additionally, the groups are of lengths of approximately integer multiples, so a velocity per vertebra may be calculated and/or compared between the groups (e.g., by diving the time of flight of one croup by that of the other group). Alternatively or additionally, the groups comprise same numbers of vertebrae. Alternatively or additionally, the groups include one or more common vertebrae.

In a preferred embodiment of the invention, the measurements may be used to detect spinal fractures, for example, compression fractures and/or cervical spine injuries, by detecting changes in velocity, waveform polarization, power spectrum, and/or other parameters of the acoustic wave. In a preferred embodiment of the invention, a determination of spinal fractures, especially of cervical spine injuries, may be performed at a site of an automobile accident, to decide on movement options.

In a preferred embodiment of the invention, the above methods of travel time determination and/or acoustic velocity determination (by dividing distance by travel time) may be applied to other bones of the body, for example, the arms, wrists, fingers, shoulders, collar bone, shin and/or jawbone. Mechanical characteristics of the bone may also be assessed from the time of flight measurements, using methods known in the art, for example, as described in the above referenced patents and publications.

Preferably, the measurement is made between points where the underlying soft tissue is thinnest. Preferably, the measuring points are at or near ends of the bone. Alternatively or additionally, at least one of the measuring points is at a middle of a bone. Preferably, only two bones (and one joint) are measured. Alternatively, two, three or more joints may be measured, for example, entire fingers, or the spine mentioned above. In some preferred embodiments of the invention, not all the joints are articulated joints, for example, cartilage joints, such as rib joints or wrist joints and/or knitted joints such as in the skull.

In a preferred embodiment of the invention, such measurements are used to detect onset, progression and/or regression of osteoporosis. Alternatively or additionally, such measurements are used to diagnose fractures or other stress-related bone defects. Alternatively or additionally, the measurements may be used to monitor a fracture healing process. Different fractures and healing states are expected to exhibit different frequency, velocity and/or attenuation profiles. Such monitoring may be effected by comparing the acoustic characteristics of two corresponding bones, by monitoring changes over time, by comparing the measurements to a table of expected values and/or by comparing different sections of the same bone.

In a preferred embodiment of the invention, such measurements may be used for identification purposes, for example, by storing relative travel times along each of five fingers of a right hand. Even if bone loss occurs it may be expected to be similar for all the fingers.

FIG. 3 illustrates various points on a body at which bone velocity may be measured in accordance with a preferred embodiment of the invention. The points are indicated with a letter, such as locations A and B described above with reference to FIG. 1C.

In an experiment, a frequency of 150 kHz was used to measure apparent velocities between points A and B in healthy patients. The term apparent velocity is used for a velocity corresponding to the straight line distance between the points divided by the time of flight. In actual bone tissue, the path of the sound is rarely straight. The apparent velocity measured was between 1800 and 1900 m/s. The thickness of soft tissue underlying locations A and B is about 1 and 1.5 cm respectively. In a preferred embodiment of the invention, the soft tissue velocity, thickness and/or travel time is estimated, to yield a more exact bone velocity. The soft tissue velocity can be estimated, for example to be between 1400 and 1500 m/s. The soft tissue thickness may be determined, for example, by measuring reflection from an underlying bone or using methods described in PCT publication WO 97/13145, the disclosure of which is incorporated herein by reference.

Another set of locations comprises a location F at an elbow and a location E at a hand. In a preferred embodiment of the invention, the location E is a knuckle, so that when a fist is made, the ultrasonic wave enters the bone at a normal angle. The knuckle is preferably used instead of the finger tip, to avoid any interaction with- and/or reflections caused by- a fingernail. In an experiment on healthy subjects using a frequency of 150 kHz, apparent velocities between 2600 and 2900 m/s were measured. The soft tissue effect is preferably ignored, since the soft tissue is very thin at points E and F (relative to length of path in the path in the bone).

Another set of locations comprises a location I and a location J at two opposing shoulders. Alternatively or additionally, one of the locations may be at the back of a neck. Another set of locations comprises a location G at a large toe and a location H at a base of an ankle. In an experiment in health subjects, a frequency of 150 kHz yielded apparent velocities of about 1900–2000 m/s.

Figure 4:
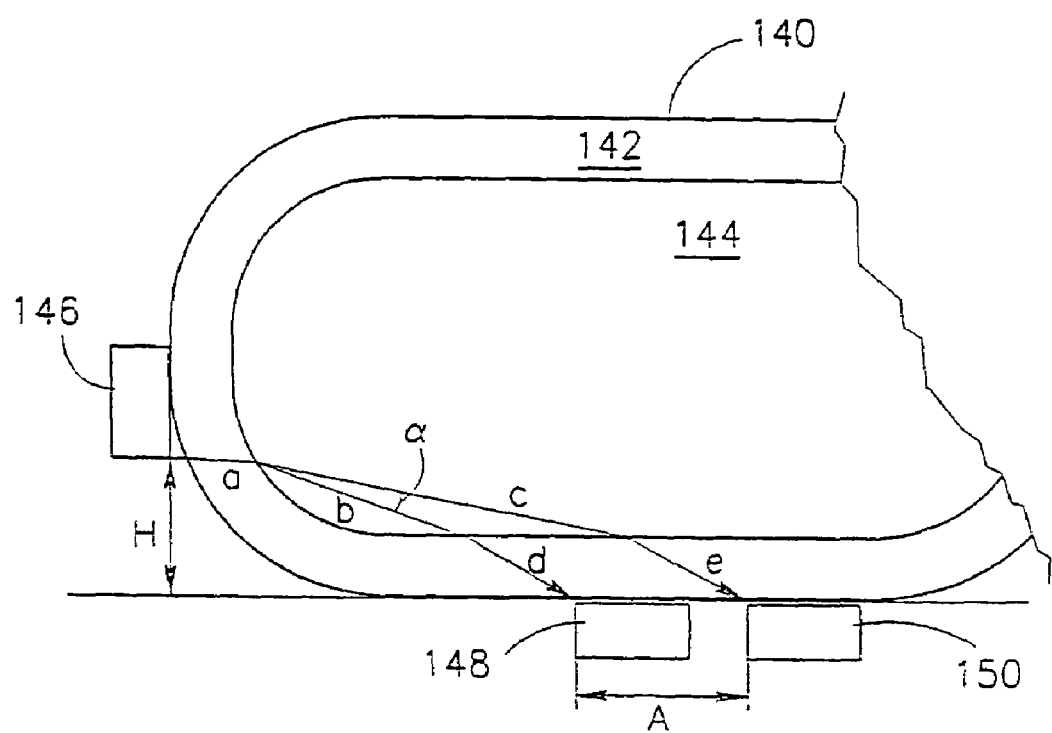
FIG. 4 is a schematic illustration of a method of determining an acoustic velocity in a bone, in accordance with a preferred embodiment of the invention.

FIG. 4 is a schematic illustration of a method of determining an acoustic velocity in a trabecular portion 144 of a bone 140, in accordance with a preferred embodiment of the invention. A transducer 146 is shown at one side of bone 140 and a pair of transducers 148 and 150 are shown at spaced away locations. It is noted that transducer 146 is substantially perpendicular to transducers 148 and 150. Ignoring intervening soft tissue, a path from transducer 146 to transducer 148 (or transducer 150) includes a short segment "a" in a cortical bone portion 142 and a long segment "b" (or "c") in trabecular bone portion 144. A third short segment "d" ("e") in the cortical bone completes the path. The frequency of the wave is preferably selected so that travel of the wave only through cortical bone is substantially attenuated, due to the small cross-section of the cortical bone. If a distance between transducer 146 and transducer 148 is relatively long compared to the distance between transducer 148 and transducer 150, paths "b" and "c" will substantially overlap and have only a small angle α between them. Path section "a" will generally be the same segment for both paths. Additionally, if transducers 148 and 150 are close together, paths "d" and "e" will pass through substantially the same thickness and/or type of cortical bone. If angle α is small, the difference in path lengths is substantially equal to the distance between transducers 148 and 150. The time of flight in trabecular bone 144 may be determined by subtracting the times of flight for the two paths. The velocity may be determined by diving the distance between the two transducers by the subtracted time of flight. Alternatively or additionally, to using two transducers, a single transducer may be moved between locations 148 and 150 and/or further locations along the bone axis. In a preferred embodiment of the invention, a horizontal distance "h" between transducer 146 and transducer 148 is made large enough so that the fastest wave does not travel only along the cortical potion of the bone.

In a preferred embodiment of the invention, the contribution of soft tissue travel time to the total travel time may be ignored for the same reasons as the effect of cortical bone because similar thickness and velocities of the soft tissue are involved for the two paths. Also, the total thickness of the soft tissue (and cortical bone) may be selected to be small relative to the trabecular bone path. Alternatively, the calculation of FIG. 4 can be applied in a situation where reference 144 represents a bone (including both cortical and trabecular sectors) and reference 142 represents soft tissue. The same considerations of overlap apply, except that the line segments "d" and "e" exit the bone at a sharper angle, to account for the differences in acoustic velocity and the difference in changing the acoustic velocities between FIG. 4 and the current described configuration.

The measurement of FIG. 4 may be applied at an ankle, with transducers 146 being at a base of the ankle and transducers 148 and 150 being along the side of the ankle bone. Alternatively or additionally, transducers 148 and 150 may be further down the foot, so that the waves travel through multiple bones. Alternatively or additionally, the measurement may be performed between an elbow acting as a point 146 and points further down the arm, near the wrist, acting as a point 148 and a point 150. Alternatively or additionally, these measurements may be performed at other points in the body where there is a significant distance between transducers 146 and 148.

Figure 5:
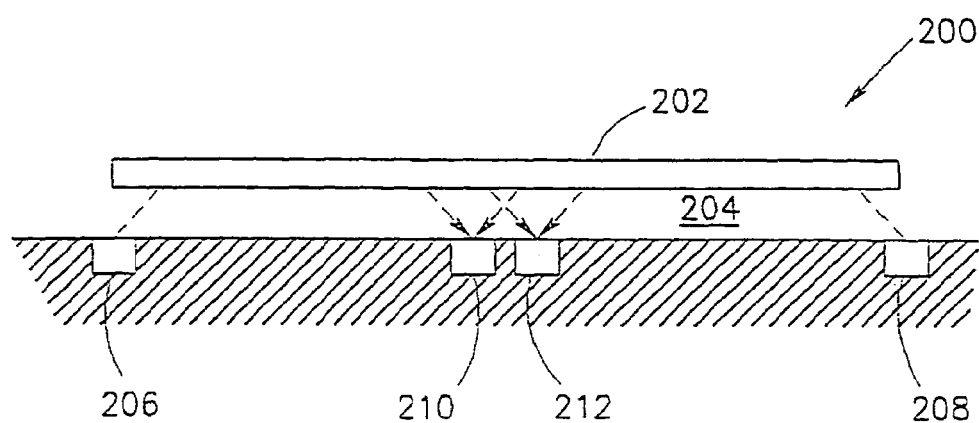
FIG. 5 illustrates a method of bone characteristics determination utilizing significantly displaced receivers and transmitters.

FIG. 5 illustrates a method of bone characteristics determination utilizing significantly displaced receivers and transmitters. Preferably, two or more sets of transmitters and receivers are used, to correct for errors in determining the characteristics, for example, errors due to the receivers not defining a line parallel to the bone. FIG. 5 shows a configuration 200 in which two significantly displaced transmitters 206 and 208 are used. Waves generated by these transmitters travel through soft tissue 204 and a bone 202, such as a femur, and again through a different part of soft tissue 204 to receivers 210 and 212. As can be see in the figure, the waves from transmitter 206 overlap for nearly all of their travel, except for a last portion. Due to the distance between transmitter 206 and the receivers, the shortest path for the two waves will usually overlap. The same is true for transmitter 208. In a preferred embodiment of the invention, the transmitters and/or receivers are slanted towards the expected path of the sound waves, to increase their gain. Alternatively, lens or other acoustic elements may be used to improve gain characteristics.

Figure 6:
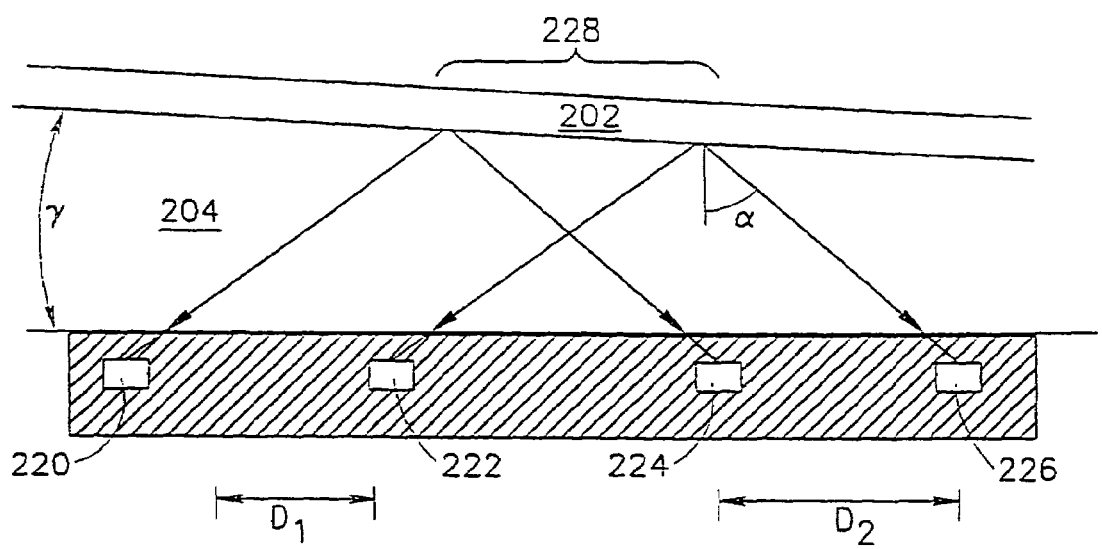
FIG. 6 is a schematic illustration of an implementation of a preferred embodiment of the present invention using the configuration of FIG. 5.

FIG. 6 is a schematic illustration of a probe utilizing of configuration 200, showing a non-parallel arrangement of the receivers to the bone and illustrating that by using two opposing transmitters and, optionally, more than one receiver-pair, various errors may be corrected, so that a more exact measurement is achieved. For clarity, the transmitters are not shown, but, preferably, one is to the right of the figure and one to the left. Four waves are shown from bone 202 to four receivers 220, 222, 224 and 226 respectively. As illustrated, these receivers are arranged in two pairs, (220, 222), having an inter-receiver distance of $D_1$ and (224, 226) having an inter-receiver distance of $D_2$. It is noted that the waves bend at the point where they pass between soft tissue 204 and the receivers, to represent changes in velocity caused by the receivers being immersed in a material having a different speed of sound from the tissue. An angle $\gamma$ is the angle between the bone surface and the soft tissue outer surface, about a segment 228 of the bone for which the measurements are being made. An angle $\alpha$ is the critical angle along which the fastest wave travels from the transmitters to the receivers and is determined by: $\sin\alpha = V_t/V_b$, where $V_t$ is the soft tissue velocity and $V_b$ is the bone velocity.

In FIG. 6, receivers 220 and 222 both detect signals from a same source, for example source 208 (FIG. 5). As seen in FIG. 6, the only difference between the paths is along segment 228 and in the length of travel in soft tissue. Preferably, but not necessarily, the soft tissue velocity is assumed the same for both receivers. Alternatively, several receiver pairs may be used so that there is a substantial overlap between soft tissue paths for different receiver pairs. In FIG. 6, both receiver pairs detect waves that can be used to analyze the characteristics in a same bone segment 228, while there is only a partial overlap in soft tissue in the volume of soft tissue traversed by the sound waves for each receiver pair. Alternatively, other configurations can be used in which a different trade-off between bone path overlap and soft tissue overlap is used. Such a trade-off can be achieved, for example, by varying the relative axial (along the path of sound from the sources) and/or transaxial (perpendicular to the path) positions of the receivers and receiver pairs. Alternatively or additionally, such trade-offs can be achieved by switching the functions of transmitters and receivers. Although a shared segment 228 is shown, in a typical application, the bone segment analyzed by each detector pair may only approximately overlap. It is generally assumed, however, that the local characteristics of the bone do not vary greatly. The intra-detector distanced $D_1$ and $D_2$ are preferably the same, however, this is not essential. In exemplary embodiments, the distance between the transmitter and the receivers is larger than 5, 10, 20 or 30 times the distance between the receivers. Also, receivers and transmitters can be on different bones, on bent portions of the bone or not all aligned relative to the axis of the bone.

In a preferred embodiment of the invention, what is utilized is a difference in arrival times of a same signal at each receiver of the pair of receivers and not the time of arrival of a signal from a sound source at a receiver. Alternatively, two consecutive signals having a known relative delay can be compared. Such signals can use, for example, a clocked source or a pulse source, for setting the delay. The difference in arrival times can be directly measured, for example, by correlating the detected signals, with the transmitted signal being continuous (and constant), pulsed or have a different type of envelope. In some continuous wave systems, the wavelength is preferably longer than the inter-receiver distance, to allow using phase based difference measurements. Alternatively, a TOF (time of flight) measurement is made for each receiver, for example based on detecting a first arriving wave at the receiver, and using a known time the pulse was generated, the measurements are subtracted to determine a time difference. For pair (220, 222), a time difference $\Delta t1$ is measured and for pair (224, 226) a time difference $\Delta t2$ is measured.

The following equations inter-relate the above defined variables and unknowns:

$$\Delta\tau_1 = D_1\left(\frac{\cos\gamma}{v_b} - \frac{\sin\gamma\cos\alpha}{v_t}\right) \quad (1)$$

$$\Delta\tau_2 = D_2\left(\frac{\cos\gamma}{v_b} + \frac{\sin\gamma\cos\alpha}{v_t}\right) \quad (2)$$

(1)

(2)

In these equations, $\Delta\tau$ and D are known or measured and $\alpha$ (critical angle), $\gamma$ (inclination angle), $V_b$ (bone velocity) and $V_t$ (soft tissue velocity) are unknowns.

Effective velocities $V_1$ and $V_2$ can be defined to aid in solving for $V_b$. Thus, by defining:

$$v_1 = \frac{D_1}{\Delta\tau_1}; \quad v_2 = \frac{D_2}{\Delta\tau_2}. \quad (3)$$

(3)

the following equations can be derived from the time of arrival difference equations:

$$\frac{1}{v_1} + \frac{1}{v_2} = 2\frac{\cos\gamma}{v_b} \quad (4)$$

$$\frac{1}{v_2} - \frac{1}{v_1} = 2\frac{\sin\gamma\cos\alpha}{v_t} = 2\sqrt{1 - \frac{v_b^2}{4}\left(\frac{1}{v_1} + \frac{1}{v_2}\right)^2}\sqrt{1 - \frac{v_t^2}{v_b^2}}\bigg/v_t$$

(4)

As an aside, it should be noted that if $\gamma=0$, $V_b$ is independent of $V_t$. These two equations can be rewritten and solved to obtain $$v_b = \frac{\sqrt{2}v_t}{\sqrt{1 + \frac{v_t^2}{v_1 v_2} - \sqrt{\left(1 - \frac{v_t^2}{v_1^2}\right)\left(1 - \frac{v_t^2}{v_2^2}\right)}}} \quad (5)$$

$$\cos\gamma = \frac{v_b}{2}\left(\frac{1}{v_1} + \frac{1}{v_2}\right)$$

(5)

One method of solving this equation set is to assume $V_t$, for example to be 1540 m/s and to use the second equation of set (5) to calculate $\gamma$. As shown below, for small angles $\gamma$, selecting this velocity as representative of a true velocity between 1480 and 1580 has a very small effect on the accuracy. Other methods of solving such equations are also known in the art.

Figure 7:
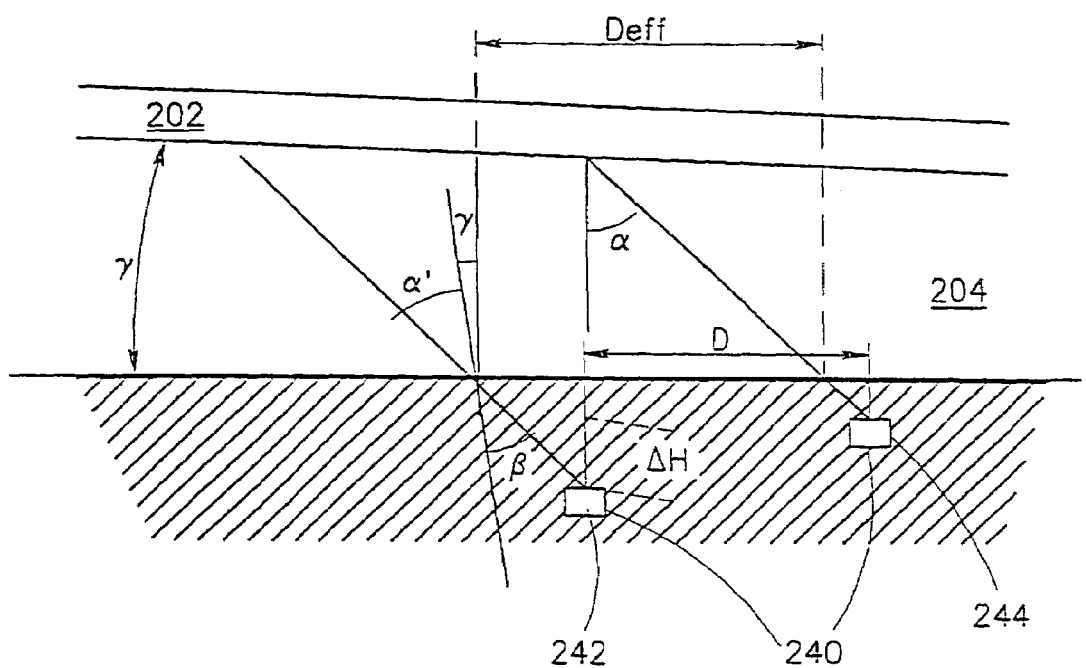
FIG. 7 is a variation of FIG. 6, in which the receivers do not define a line parallel to a surface of the soft tissue.

FIG. 7 illustrates a variation of FIG. 6, in which the receivers do not define a line that is parallel to a surface of the soft tissue ("displaced receiver") and shows details of one displaced receiver pair 240, comprising receivers 242 and 244. Unlike FIG. 6, receiver 244 and receiver 242 are not parallel to the surface of soft tissue 204. A distance $\Delta H$ describes the relative elevation of one receiver relative to the other. Angles $\alpha'$ and $\beta$ can be defined, to transform the example of FIG. 6 into the example of FIG. 7: $\alpha'=\alpha-\gamma$ and $\sin\beta=V_p\cdot\sin\alpha'/V_t$, where $V_p$ is the speed of sound in the material in which the receivers are embedded.

By expansion, it can be shown that the angle $\beta$ satisfies the following equation:

$$\sin\beta = \frac{v_p}{v_b}\cos\gamma - \frac{v_p}{v_t}\sin\gamma\sqrt{1-\frac{v_t^2}{v_b^2}} \quad (6)$$

(6)

An effective distance $D_{eff}$ and an effective time delta $\Delta\tau_{eff}$ defined below can be used in the equations of FIG. 6, which were defined for a non-displaced receiver example. Typically, there is one set of $D_{eff}$ and $\Delta\tau_{eff}$ for each receiver pair.

$$D_{eff}=D+\Delta H \, \text{tg}\beta. \quad (7)$$

$$\Delta\tau_{eff}=\Delta\tau-\Delta H/(v_p\cos\beta) \quad (8)$$

FIG. 7 shows only one pair of receivers, typically two pairs will be used, with one or both being displaced receiver pairs.

The resulting set of equations may be solved in many ways. One suggested iterative method comprises:

(a) assume $\Delta H=0$.
(b) compute $V_b$ and $\gamma$ based on the FIG. 6 equations (equations (3) and (5)), setting $D_{eff}=D$ and $\Delta\tau_{eff}=\Delta\tau$, for both pairs of receivers.
(c) using y and $V_b$, calculate $\beta$, $D_{eff}$ and $\Delta\tau_{eff}$ using the FIG. 7 equations (6–8), for both pairs of receivers. And
(d) reiterate computing $V_b$ using the more precise $D_{eff}$ and $\Delta\tau_{eff}$.

Typically, two or three iterations are required to reach a calculation precision of better than 0.1% or even 0.01%, for $\gamma<5°$ and $\Delta H<0.1$ D, the iterations may be stopped based on their number or based on achieving a desired precision. Alternatively, other solution methods may be used.

In a simulation performed for an embodiment according to FIG. 6, a precision of better than 0.1% was achieved for $\gamma<5°$, if a true $V_t$ is between 1480 and 1580 m/s. For larger inclinations, a probe having an opposite inclination may be used, so that the effective $\gamma$ is closer to zero.

In a preferred embodiment of the invention, different bones have different allowed inclination angles, determined, for example, based on an expected noise and/or error level. In some preferred embodiments of the invention, the measurement system generates a signal (e.g., a beep or a red light on the probe) if the approximately determined inclination angle is larger that the value allowed for the particular bone being measured. In some embodiments, the velocity will not be determined in such a case. The signal can cause the user to reorient the probe, for example to push it deeper into the flesh. Additionally or alternatively, other conditions that cause a large error, such as high noise conditions may be signaled to the operator so that he can change the measurement method accordingly.

In the above description, the receivers and transmitters are substantially in a same plane with the bone. However, this is not essential. What is most often desirable is that the receiver pair is arranged to be coplanar with the near path of the wave in the bone, so that there is a maximum overlap between the paths of the two receivers. However, even this is not essential. In one preferred embodiment of the invention, the line connecting the receiver pair is arranged to be perpendicular to a line connecting the source and the receiver pair, or at a different angle. One such arrangement has one receiver coplanar with the near path and one receiver perpendicular to the plane of the coplanar receiver and the near path. As used herein the near path is the portion of path of acoustic waves near the receivers and in which variations between the paths to the two receivers are found. In the far portions, the waves generally overlap or travel completely separate paths.

In a preferred embodiment of the invention, the determination that the receivers are in a desired configuration is achieved by determining the receiver orientation at which a local or global minimum or maximum velocity is determined and/or based on other analyses of the velocities determined for different angles. Thus, in some implementations, the determined bone velocity is actually an effective velocity rather than a real velocity. However, since the effective velocity is reproducible, it may be used to compare different patients or a same patient over time. In some cases, a normalized velocity or an otherwise processed travel time may be used instead of the effective the velocity and usually in a way equivalent thereto. Using non-coplanar configurations, some trans-axial characteristics of the bone may also be determined. Alternatively or additionally, the two sources are not opposite each other, but define a non-180° angle with the receivers. However, as noted above, the parameter of interest may be that the two near paths from the two sources are not coplanar, but define an angle, such as 120°, 150° or 170° between them. Such angles may be achieved and useful, for example in the skull.

Also, as noted above, the transmitters and receivers can be swapped or a single pair of receivers can be used. Possibly, a plurality of receivers, for example arranged in a ring, is used to detect signals from a same source or sources. Such a ring may be used to select a desirable orientation of the receiver pair to the near path, without requiring motion of the receiver pair. Thus, a variety of trans-axial characteristics can be determined and some amount of angle independence can be achieved. It is noted that, in general, the sources are far enough away from the receivers so that the differences between what the receivers detect is mainly caused by local variations. Thus, the exact location of the sound sources may be of no interest. In one embodiment, an imaging probe, with appropriate software/hardware processing circuits is used for analyzing received signals, while the acoustic source may be a separate "thumper" or sound generating probe.

In one preferred embodiment of the invention, an acoustic source, optionally self powered and without any connecting wires, is attached to the patient, for example using a strap or adhesive. It should be noted that a wide range of sound sources may be used, including narrow frequency band and wide frequency band sources. Some exemplary sources include piezoelectric elements, electro-magnetic vibrators and mechanical thumping (e.g., with a hammer). It should be noted that a hammer (or other hard object) can be hit against the body as well as being hit against an object in contact with a limited portion of the body, e.g., a table on which the patient stands.

Although mainly velocity has been described as the desired measurement, other bone characteristic can be determined. In one example, the frequency profiles of the signals detected at two receivers can be compared to determine a frequency attenuation profile of the bone.

The above method of acoustic velocity determination is especially useful for long bones, such as the femur or for measurements along long portions of the body, such as an entire arm. Other situations where such measurements are useful are
- (a) when the bone portion to be measured and/or the encompassing bone are short, such as the fingers;
- (b) when the bone is rounded (such as the ankle), so one of the transmitter and the receiver is at the side on the bone and the other at the back;
- (c) when the bone is small relative to the speed of sound in the bone, such as in the ankle (or in non-bone tissues, such as in teeth or between teeth); and/or
- (d) when it is desired to avoid a parasitic signal through the probe or the skin (as the transmitter can be very far from the receivers, such parasitic signals are attenuated below the background noise level).

However, these methods may also be advantageously applied in other configurations, for example where the receiver (and wavelength) is small relative to the soft tissue thickness. e.g., for thinly covered bones.

In a preferred embodiment of the invention, the ultrasonic bone velocity measurement may be restricted to substantially a joint area, for example, from just above an elbow to just below an elbow. In a preferred embodiment of the invention, the measurement apparatus comprises a "V" shaped apparatus with a transducer at an end of each arm of the "V" and with a variable base angle (one being a receiver and one a transmitter). Alternatively, a "U" shaped apparatus, as described above, may be used. Alternatively or additionally, a grid type probe is used for velocity measurements in bone and/or joints, in which individually excitable (and/or receiving) portions are available on a flexible or a rigid substrate.

In a preferred embodiment of the invention, such bone and/or joint velocity measurements are performed at multiple joint positions. Preferably, these multiple measurements are used since the path may be expected to include different parts of the bone, depending on the joint angle. Alternatively or additionally, the multiple measurements accommodate different thicknesses of joint tissue between the bones.

The present invention has been described in terms of preferred, non-limiting embodiments thereof. It should be understood that features described with respect to one embodiment may be used with other embodiments and that not all embodiments of the invention have all of the features shown in a particular figure. In particular, the scope of the invention is not defined by the preferred embodiments but by the following claims. Section titles, where they appear are not to be construed in limiting subject matter described therein, rather section titles are meant only as an aid in browsing this specification. When used in the following claims, the terms "comprises", "comprising", "includes", "including" or the like means "including but not limited to".

What is claimed is:

1. A method of determining an acoustic velocity in a bone, comprising:
   transmitting, from a location adjacent a first in-vivo bone, an acoustic wave having a wavelength about the same or smaller than a cross-section of the bone, which cross-section is perpendicular to a main travel direction of said acoustic wave in said bone;
   receiving said acoustic wave at a location adjacent a second in-vivo bone; and
   determining at least one acoustic characteristic of at least a portion of at least one of the first and second bones, from a travel time of said wave through said first and second bones and at least one joint between said bones, wherein said acoustic characteristic comprises at least an acoustic velocity.

2. A method according to claim 1, wherein said locations have an unknown positional relationship.

3. A method according to claim 1, wherein said locations have a known positional relationship.

4. A method according to claim 1, wherein said receiving and said transmitting comprise receiving and transmitting using mechanically coupled acoustic elements.

5. A method according to claim 1, wherein said receiving and said transmitting comprise receiving and transmitting using mechanically uncoupled acoustic elements.

6. A method according to claim 1, wherein said acoustic wave has a frequency of at least 20 kHz.

7. A method according to claim 1, wherein said acoustic characteristic comprises acoustic velocity.

8. A method according to claim 1, wherein said acoustic characteristic comprises acoustic attenuation.

9. A method according to claim 1, wherein said acoustic characteristic comprises polarization properties.

10. A method according to claim 1, wherein said at least one acoustic characteristic is determined for a plurality of wavelengths, to estimate a frequency dependent variation thereof.

11. A method according to claim 1, wherein the at least one joint is articulated.

12. A method according to claim 1, wherein said first and second bones are interconnected by at least a third bone and wherein said at least one joint comprises at least one joint interconnecting said first bone and said at least third bone and at least a second joint interconnecting said at least third and said second bones.

13. A method according to claim 12, wherein said at least a third bone comprises at least two bones interconnected by a joint through which the wave travels.

14. A method according to claim 1, wherein said wave travels between an elbow and a finger.

15. A method according to claim 1, wherein said wave travels between an elbow and a knuckle.

16. A method according to claim 1, wherein said wave travels between a knee and an ankle.

17. A method according to claim 1, wherein said wave travels between a trochanter and a pelvis.

18. A method according to claim 1, wherein said wave travels between two hips.

19. A method according to claim 1, wherein said wave travels along a rib.

20. A method according to claim 1, wherein said wave travels along a portion of a skull.

21. A method according to claim 1, wherein said bones comprise spinal vertebra.

22. A method according to claim 1, wherein receiving the acoustic wave comprises receiving at least a second acoustic wave, which second wave has a path including at least one shared path portion in bone with said first wave.

23. A method according to claim 22, wherein the two waves are received using a single receiver and are generated at two different locations.

24. A method according to claim 22, wherein the two waves are received using two receivers and are generated at a single location.

25. A method according to claim 24, wherein a line interconnecting said two receivers is not parallel to a surface of bone underlying the two receivers.

26. A method according to claim 22, wherein said travel time comprises a relative travel time of said two waves.

27. A method according to claim 22, wherein said two waves are generated simultaneously.

28. A method according to claim 22, wherein said two waves are generated as a single source wave.

29. A method according to claim 22, wherein said two waves are generated at a time delayed relative to each other.

30. A method according to claim 1, comprising repeating said transmitting and said receiving for at least a second acoustic wave, traveling in a direction opposite a traveling direction of said wave, to determine local acoustic bone characteristics at an area which is traversed by both of said waves.

* * * * *